United States Patent
Bahnson et al.

(10) Patent No.: US 6,830,931 B2
(45) Date of Patent: Dec. 14, 2004

(54) METHOD AND APPARATUS FOR MONITORING OF PROTEINS AND CELLS

(75) Inventors: Alfred Blalock Bahnson, Pittsburgh, PA (US); Douglas J. Koebler, Irwin, PA (US); Charalambos N. Arthanassiou, Athens (GR); Raymond K. Houck, Oakmont, PA (US); Kris Sachsenmeier, Pittsburgh, PA (US); Lei Qian, Oakmont, PA (US)

(73) Assignee: Automated Cell, Inc., Pittsburgh, PA (US)

( * ) Notice: Subject to any disclaimer, the term of this patent is extended or adjusted under 35 U.S.C. 154(b) by 0 days.

(21) Appl. No.: 10/032,661

(22) Filed: Oct. 26, 2001

(65) Prior Publication Data

US 2003/0082818 A1 May 1, 2003

Related U.S. Application Data

(63) Continuation-in-part of application No. 09/904,144, filed on Jul. 12, 2001.

(51) Int. Cl.[7] .............................................. G01N 33/48
(52) U.S. Cl. ........................ 436/63; 436/10; 436/529; 436/530; 436/172; 436/166; 435/24; 435/4; 435/29; 435/30
(58) Field of Search ................................ 436/63, 10, 529, 436/530, 172; 435/24, 4, 29, 30, 7.1

(56) References Cited

U.S. PATENT DOCUMENTS

| | | | | |
|---|---|---|---|---|
| 4,161,514 A | * | 7/1979 | Casey | 435/34 |
| 6,008,010 A | * | 12/1999 | Greenberger et al. | 435/41 |
| 2003/0017522 A1 | * | 1/2003 | Bahnson | 435/24 |

* cited by examiner

*Primary Examiner*—Jill Warden
*Assistant Examiner*—Sam P. Siefke
(74) *Attorney, Agent, or Firm*—Ansel M. Schwartz

(57) ABSTRACT

An apparatus for monitoring proteins and cells. The apparatus includes a plate having wells in which cells are disposed. The apparatus includes means for analyzing the effect or proteins and other biological and chemical moieties on the cells. A method for monitoring of proteins and cells. A method for analyzing a cells. An apparatus for aligning light in a well of a plate for holding cells. A method for lighting a well. A method for determining a condition of a cell. An apparatus for indicating a condition of a cell. A method for establishing a focus profile of a plate having wells for holding cells. A method for manipulating cells. An apparatus for manipulating cells.

8 Claims, 11 Drawing Sheets

IN FOCAL PLANE 1, CELL(1) IS IN FOCUS

IN FOCAL PLANE 5, CELL(2) IS IN FOCUS

METHOD AND APPARATUS FOR MONITORING OF PROTEINS AND CELLS

The present invention is a continuation-in-part application claiming priority from U.S. patent application Ser. No. 09/904,144, filed on Jul. 12, 2001.

FIELD OF THE INVENTION

The present invention is related to the analysis and study of proteins and cells. More specifically, the present invention is related to the analysis and study of the effects of proteins and other biological and chemical moieties on cells in wells of a plate where the environment of the cells is manipulated and techniques facilitate the identification and tracking of the individual cells and population of cells in the wells.

BACKGROUND OF THE INVENTION

The analysis of the effects of proteins and other biological and chemical moieties on cells is an important field for the development of improved therapeutics for human health. The analysis of human and other types of cells requires sophisticated analysis methods. This patent application is directed at the improvement of the protein and cellular analysis methods used fro drug discovery and gene and protein function determination.

Establishing protein function is a key part of any drug discovery effort. Whether performing target discovery, prioritization or validation, screening for novel protein therapeutics, lead optimization, or discerning mechanism of action, the demonstration of functional relevance is essential. The human genome comprises approximately 35,000 genes. These genes produce approximately 300,000 to 500,000 proteins in the human body. The sequence of genes that make up the human genome is known, but only about 20% to 30% of this genome has functional definitions of what the specific gene and its protein products produce in health and disease. In the history of the pharmaceutical industry, drugs have acted upon only 500 protein targets in the human body. Over the next few years, the industry will have 100 to 200 times more protein targets produced through genomics and proteomics efforts. A significant opportunity exists to identify, prioritize, and validate these new protein opportunities through discovering their protein function. This function knowledge can be patented.

Most genomic and proteomic efforts infer disease-linked function by methods based upon homology such as protein—protein association (e.g. two hybrid systems or mass spectroscopy) or disease-linked expression profiling (e.g. 2D gel electrophoresis or various nucleic acid or protein chip technologies). The challenge of demonstrable functional relevance remains an inevitable downstream step in the development of promising candidates from approaches where function is only inferred. The return on any investment in discovery efforts can be lost when a particularly promising candidate has a weak functional role in a disease-relevant system. Despite these drawbacks, inference-based proteomics has been the mode of choice because of the relatively low throughput of various functional determination systems based upon animal models and gene knock-out technologies.

The technology described herein maximizes the efficiency of proteomic drug discovery by establishing protein function. By screening at the level of protein function itself, loss of time and investment due to subsequent failure in a functional assay is minimized. Putative protein targets are discovered, prioritized and pre-validated at the screening step. A key strength of the technology are biochemical and biological assays with the capacity for multiple assay endpoints with a high degree of quantitative sophistication.

Since the assay created by the technology are nondestructive, a single assay well yields kinetic information about protein-related behavior of a given set of cells over assay periods of seconds to weeks. Subtle changes in cellular response to proteins over time are detected and quantified at resolutions as low as five seconds. The analyses are performed within the same well, on the same set of cells at a single cell resolution. Other endpoints include apoptosis, proliferation, changes in cell morphology, cell—cell interactions, protein expression, and other phenotypical changes as listed in Table 1.

The capacity for measuring protein effects upon co-cultures of multiple types of biologically relevant cell type combinations is created. The number and combination of different cell types that can be assayed is determined by the ability of the image analysis software to distinguish each cell type. Delimiters include cell morphology, motility, fluorescent protein expression, antigen elaboration, as well as assay prehistory.

Sophisticated image analysis algorithms make the quantitation of individual cell behavior possible. This means that each cell in an assay is being observed individually for its response to an exogenously added or transfected protein or protein combination. Quantitation at single cell resolution eliminates the masking of subpopulation effects. This unparalleled quantitative resolution, combined with the capacity for extended kinetic assays, ensure that subtle or short-lived cellular responses to proteins are not overlooked.

SUMMARY OF THE INVENTION

The present invention pertains to a method for analyzing the effects of proteins and other biological and chemical moieties in cell (s). The method comprises the steps of placing the cell in a solution that suppresses non-biological movement of the cell. There is the step of using time-lapse imaging to analyze motility of the adherent and non-adherent cell(s) in the solution.

The present invention pertains to a method for analyzing the effects of proteins and other biological and chemical moieties in cell(s). The method comprises the steps of placing cells in a solution having a methyl cellulose concentration on a plate having between 6 and 1,536 wells with corresponding volumes of approximately 1 to 4% of the total volume of the solution. There is the step of imaging the cells over time.

The present invention pertains to an apparatus for aligning light in a well of a plate for holding cells. The apparatus comprises a top portion that is adapted to hold to the plate. The apparatus comprises a bottom portion connected to the top portion that is adapted to extend into the well below a meniscus in the well. The top and bottom portions are made of a transparent material that lets light pass through it and be distributed evenly throughout the bottom of the well.

The present invention pertains to a method for lighting a well. The method comprises the steps of placing a first portion of a light alignment apparatus onto a plate having wells so a second portion of the light alignment apparatus extends into a well and below a meniscus in the well. There is the step of directing light onto the first portion that is evenly distributed by the second portion to the bottom of the well.

The present invention pertains to a method for determining a condition of a cell, both in a normal state and in a state where the cell has been effected by the addition of a protein or other biological or chemical moiety. The method comprises the steps of placing a bead coated with a first material in a well of a plate. There is the step of identifying a second material released by a cell in the well by the second material reacting with the first material.

The present invention pertains to an apparatus for indicating a condition of a cell. The apparatus comprises a bead. The apparatus comprises a layer of a first material that reacts with a second material that is released from the cell when it is the condition, the layer coating the bead.

The present invention pertains to a method for establishing a focus profile of a plate having wells for holding cells. The method comprises the steps of taking images at focal points above a current setting and below the current setting. There is the step of applying an image processing sequence to arrive at a focus for the plate.

The present invention pertains to a method for manipulating cells. The method comprises the steps of guiding a pipette with a controller to a predefined position in a well of a plate having a predetermined cell. There is the step of aspirating the cell with the pipette from the well. There is the step of placing the cell at another location with the pipette at the guidance of the controller.

The present invention pertains to an apparatus for manipulating cells. The apparatus comprises a plate having wells that hold cells. The apparatus comprises a controller. The apparatus comprises a pipette means for aspirating a well and controlled by the controller which guides the pipette means to a predetermined position in a well of the plate having a predetermined cell to aspirate the cell with the pipette from the well and place it at another location.

The present invention pertains to an apparatus for monitoring the effects of proteins and other biological and chemical moieties on cells. The apparatus comprises a plate having wells in which cells are disposed. The apparatus comprises means for causing each cell to move to a corner of each well. The causing means is connected to the plate.

The present invention pertains to a method for monitoring the effects of proteins and other biological and chemical moieties on a cell. The method comprises the steps of loading one cell in each well of a plurality of wells of a plate. There is the step of causing each cell to move to a corner of each well.

BRIEF DESCRIPTION OF THE DRAWINGS

In the accompanying drawings, the preferred embodiment of the invention and preferred methods of practicing the invention are illustrated in which.

DETAILED DESCRIPTION

Figure 3A:
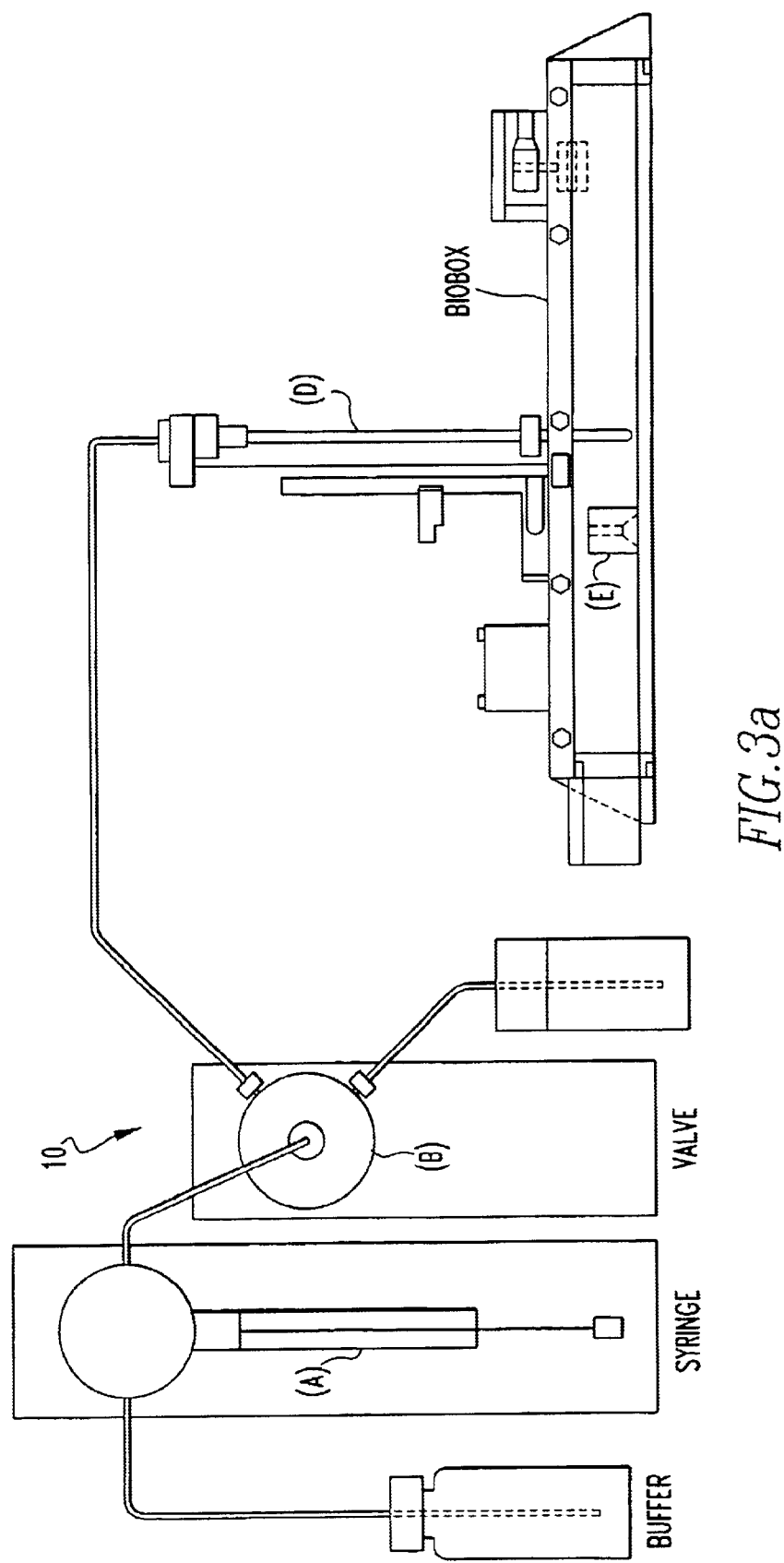
FIG. 3a is a schematic representation of the fluidics connected to the biobox.

Referring now to the drawings wherein like reference numerals refer to similar or identical parts throughout the several views, and more specifically to FIG. 3a thereof, there is shown an apparatus for manipulating cells. The apparatus comprises a plate having wells which hold cells. The apparatus comprises a controller. The apparatus comprises a pipette means for aspirating a well and controlled by the controller which guides the pipette means to a predetermined position in a well of the plate having a predetermined cell to aspirate the cell with the pipette from the well and place it at another location.

The present invention pertains to a method for analyzing the effects of a protein or other biological or chemical moiety on a single cell or a population or subpopulation of cells. The method comprises the steps of placing the cell(s) in a solution. There is the step of using time lapse imaging to analyze motility and other morphological phenotypical parameters of the cell of the cell(s) in the solution. A listing of the various parameters is giving in Table 1. Table 1 includes the cellular parameters currently being mathematically modeled and calculated. Yet, any cellular event or phenotypically change that can be imaged can be mathematically calculated and analyzed by these techniques.

The present invention pertains to a method for analyzing a cell. The method comprises the steps of placing the cell(s) in a solution which suppresses the non-biological motion of the cell(s). The method comprises the steps of placing cells in a solution having a methyl cellulose concentration on a plate 16 having between 6 and 1,536 wells 14 with corresponding volumes of approximately 1 to 4% of the total volume of the solution. There is the step of imaging the cells.

The present invention pertains to a method for monitoring a cell. The method comprises the steps of loading one cell, or a population of cells, in each well 14 of a plurality of wells 14 of a plate 16. There is the step of causing each cell(s) to move to a corner of each well 14.

Preferably, after the causing step, there is the step of locating each cell in each well 14 with a microscope 18. The causing step preferably includes the step of tilting the plate 16. Alternately, the causing step includes the step of centrifuging the plate 16. Alternately, the causing step includes the step of tilting the microscope 18.

Preferably, the locating step includes the step of presetting focus of the microscope 18 to the corner of each well 14. The locating step preferably includes the steps of placing beads 20 in the wells 14, and focusing the microscope 18 on the bead 20 in each well 14 to facilitate the focus of the microscope 18 on the cell in each well 14. The locating step preferably includes the step of imaging each well 14 based on predetermined times or predetermined events. The predetermined events can be based on, for example, the division, phenotype expression, or morphology of a cell or other parameters as further detailed in Table 1.

Preferably, the focusing bead 20 step includes the steps of focusing on each bead 20 visibly, focusing on each bead 20 using fluorescence of the bead 20, going to each corner of each well 14, and performing multiple object tracking on the cell in the corner. After the locating step, there is preferably the step of removing each well 14 from scanning where no cell is detected. The locating step can include the step of taking a focal stack of a position in at least one well 14.

In the operation of the invention, the plate 16 is first loaded with 1 cell per well 14. This method involves a number of manual methods to separate stem cells from a sample of blood, isolate cells by a specific marker using magnetic separation, again manually, then the cells are sent to a fluorescent activated sorter (FACS from Becton Dickinson, 1 Becton Drive, Franklin Lakes, N.J. USA 07417) to isolate stem cells, a very small population of the original sample. The cells are then diluted and added to a micro assay plate 16 with a multi tip pipette. This procedure is all performed outside the apparatus. The plate 16 is then spun in a centrifuge. The cells are pulled to the bottom of the well 14 and any trapped air in the well 14 is pushed to the top of the well 14. The cells are next tilted about ⅜ of an inch (A) in an incubator 24. The tilt causes the cells to move to one corner of the well 14. In about 2 to 3 days (or shorter depending upon the viscosity if the medium) all the cells are in the corner of the well 14, ready to be placed with the apparatus. A faster method to move the cells to the corner of the wells is to spin the plate 16 horizontally in an incubator 24, overnight to encourage cell motion to a corner of each well 14. This method takes about a day. The cells are then placed on the microscope 18, by the operator. It is much easier to locate the cells since they are in the corner of a well 14.

Another method to move the cells to the corner of the wells is to tilt the whole microscope 18. A table is placed under the microscope 18 and the whole microscope 18 is tilted, micro assay plate 16 and all. This keeps all the cells in the view field, in the corner. If some of the cells are not in the corner when the experiment starts, they will move to the corner and later can be added to the experiment. The tilting of the microscope 18 may also be automated, to move the tilt in the well 14, based on a method to look at cell motion with/without the effect of gravity. A sensitivity of the cells to the balance of the plate 16 has been observed. A preset focus to the corner of each well 14 in the 384 well 14 plate 16 can be included.

The operator places a micro assay plate 16 in position. The apparatus moves the plate 16 to a specific position. The operator focuses on a point in the well 14 manually. The apparatus then moves the microscope 18 to locations in wells 14 and focuses the microscope 18. The operator locates a cell in the view field and performs the final adjustment to the focus. This preset focus also reduces the set up time for starting an experiment.

Visible and/or fluorescent beads 20 can be added to some of the wells 14. These beads 20 are small in size, 1 to 10 microns in diameter, and are added manually in a solution or automatically placed by a liquid dispensing robot. The robot has the beads aligned in a tube to a needle. The robot moves the needle to a well whereupon a pump connected to the tube pumps a predetermined amount of fluid into the tube, raising the pressure enough to cause one bead to be released from the needle into the well. This is repeated as often as necessary for that well, or additional wells. The beads are made of polystyrene, and are obtained from Polysciences, Inc. 400 Valley Road, Warrington, Pa. 18976). The beads 20 settle on the bottom of a well 14. The visual focus of a bead 20 is much easier than focus of a cell. Some of the beads 20 are also fluorescent, and can be focused in the fluorescent condition. The focus sensitivity in fluorescence is very sensitive and can be used to automate the focus or refocus of a plate 16. By adding beads 20 at the four corners of a micro assay plate 16, (possibly more or less locations), and knowing the typical focus profile, the focus positions for each plate 16 added to the instrument can be determined. If the focus profile of a plate 16 is not known, more points are needed, but the same principle holds. The focus can be determined, real time, by adding adjustment by the apparatus, automated, based on the size and edge characteristics of the cell in the view field, the focus will adjust over time, as the cell changes shape or position in the well 14. The digital image of the cell can be processed with a program such as Image-Pro Plus from Media Cybernetics 8484 Georgia Ave., Silver Spring, Md. 20910. Cells that are out of focus do not have a sharp edge, creating objects that are larger or not easily extracted from the image. By taking images at focal points above and below the current setting, then applying an image processing sequence, the object with the sharpest edge (in focus), will produce an object with similar features to previous images taken, for example, similar area. An out of focus image will produce larger or smaller objects within the image. Adjusting the focus to produce objects within a range, based on area, or some other morphological characteristic, will keep the system in focus.

Since the plates used in the device are manufactured by a number of companies, the focus profile varies, manufacturer to manufacturer. But, the variation from the same manufacturer is repeatable since they are molded. This focus profile of a plate, once determined can be reused, to simplify the start up procedure for the instrument. Given the profile, for any position that the operator locates in x and y, the z position (focus) will already be known, so only fine focus will be required. The other issue is plate removal then reintroduction. Since the plate cannot be returned to exactly the same position x, y, and z (focus), if the profile is known, moving to 3 positions on the plate, you can transform all the previous positions to the new locations.

The present invention pertains to a method for establishing a focus profile of a plate 16 having wells 14 for holding cells. The method comprises the steps of taking images at focal points above a current setting and below the current setting. There is the step of applying an image processing sequence to arrive at a focus for the plate 16.

Preferably, there is the step of storing the focus profile. There is preferably the step of determining that a second plate 16 is a same type as the plate 16 that has previously had a focus profile identified. There is the step of reusing the focus profile that has been stored with the plate 16 with the second plate 16. Preferably, there is the step of moving to three positions on the second plate 16, and transforming previous positions stored of the plate to new locations on the second plate 16.

These methods will enable the effective analysis of 1536 wells 14 in plates 16, with an automated setup. The controller will set up the focus, by going to the wells 14 where the beads 20 are located and focus, first in visible, then fine focus using fluorescence. The microscope 18 will then go to each corner of a well 14 where the cell should be and start multiple object tracking. The cells should be in the corners of the wells 14. The cell is detected by contrast in light. The cell blocks the light, and since nothing else but a cell or cells are in the well, the absence or decrease in light at a location in the field of view of the camera indicates the cell's presence. If no cell is detected by the software, after a defined number of scans (see definition of scans below), that well 14 will be removed from scanning and image processing, to save time. Typically, ⅓ of the wells 14 have a single cell in the well 14, so ⅔ of the wells 14 will ultimately be rejected. If a population of cells is used in the well plate, then typically, all wells will have cells. The above methods also apply to wells with a population of cells in them.

Another feature of the apparatus is the ability to take a focal stack of a selected position or positions in a well 14, during a scan of the plate 16. A scan is defined as taking images of each well 14 the operator has selected at a predefined time. A scan can include all wells within a plate or a selected subset of the wells. A focal stack is a predefined set of focus points in the Z or vertical dimension. If cells are in a clear or translucent matrix (methylcellulose or agarose), images can be taken at different focal planes up through the matrix. The cell is then detected and a 3D image produced of the cell as it moves through the matrix. As the number of wells 14 increases in an experiment, some of the wells 14 have cells that do not move as much or are adherent, (little motion), so these wells 14 do not need to be imaged as often. The apparatus has the capability of skipping wells 14 on certain scans, image a well 14 once an hour instead of the typical every 15 minutes. This skipping can also be tied to a biological event, such as cell division. It is known that a cell will slow down and round up before a 'typical' division, so if the software detects this event, the scan rate for that cell can be increased to get more information at the time of the event. The digital image can be processed and objects extracted with an image processing program such as Image-Pro Plus. One of the morphological characteristics of the objects extracted from the image is the Aspect ratio, (length divided by width). If an object is close to round, the Aspect ratio is close to 1. This indicates a cell is close to division. There are also other morphological characteristics that can indicate a cell is close to division: size may slightly increase, roundness, and or lumpiness (texture in the object). By observing cells that have divided, a set of morphological characteristics will indicate when a cell is close to division.

Multi-processing, that is, permitting unique processing for a given well 14 or cell within a well 14. The operator typically selects a cell (or population of cells) in a micro assay plate 16 well 14 to track. The operator decides to track that cell. In the same well 14, the operator may decide to take images of the corner of the well 14, but not track cells, that is another location to scan. It is also possible to process any number of cells within a well 14 and process them differently in regard to imaging, such as detect division and stain the cells to detect phenotypical outputs, but not to stain if the other cell divides.

If there is, for example, more than one cell type in the well 14, the controller has the ability to have multiple experiments going on at the same time. Different types of cells in wells 14, with different growth factors, different number of cells in a given well 14, as well as different types of processing, different proteins added or transfected into the cells can all be done within the same well or in different wells within the same plate. This is called combinatorial biology, where multiple experiments are conducted in parallel with highly multiplexed outputs. One well 14 may be processed by visible light tracking, a second is not tracked, just images are taken, a third well 14 is being tracked by fluorescence, and a fourth a focal stack is taken to look at 3D motion.

The imaging step can also includes the step of imaging the cell(s) in the first well with viable light, then imaging the cell(s) in the well by fluorescent light, and overlaying the images. All the parameters in Table 1 can then be determined. At a later time (1 second, 1 day or 1 week), the imaging of the well can be performed again and thus a time series of visible and/or fluorescent images created. This time series of images can be analyzed for any or all of the parameters in Table 1, including motility, morphology, protein expression and/or phenotypical changes, to create a kinetic analysis of the cellular performance and how proteins or other biological and/or chemical moiety or multiple moieties effect cell performance. This time dependent (i.e. kinetic) analysis can be based upon only the viable images or only on the fluorescent images, or on the combination of both types of images. One skilled in the art will realize that other types of imaging, such as confocal, DIC, electron, or atomic, can also be applied to created kinetic based analysis of the effects of proteins and other type of biological and chemical moieties on cellular performance. This technology can be applied to other types of cells including human, mouse, other animals, fish, bacterial, yeast and plant.

The addition of proteins or other biological and/or chemical moiety or multiple moieties to the cells can be done by a number of methods including 1) the direct adding of the moiety to the cell(s) in the well, 2) the transduction or transfection of genes or proteins into the cells that are subsequent added to the well, or 3) the adding of a second type of cells to the first cells in the well wherein the additional cells secrete or in some other manner emit the moiety into the well or come into contact with the first cells and transfer the moiety to the first cells.

The cell environment has been improved by adding a humidity generator (A). The cells in a micro assay plate 16 must be kept at 37 deg C. in CO2 at 5% to maintain the PH of the liquid and the concentration of the solution around the cell must be maintained. The solution in each well 14 should not evaporate, or the concentration of the growth factor in the solution changes. The Biobox on the microscope 18 is a heated box controlled to 37 deg. C., with CO2 control, used to maintain a constant temperature and environment for live cells. To reduce evaporation in the Biobox, a humidity generator introduces water vapor to the environment.

The environment above the cell, must be humid, to control evaporation. Tests with an ultrasonic generator produced too much humidity and unwanted condensation which interference with optical detection. Using a heated container of water, this increased the humidity to levels equal to a basic incubator 24 eliminates this problem. The wells 14 actually evaporate less fluid than if placed in a standard laboratory incubator 24 with the lid on the plate 16. In cases where the lid has to be off the plate 16, evaporation can still occur. Adding filter paper (B) to the top of the well 14, or a gel lid (C), such that a needle can still transfer liquid at a specified event, keeps the fluid level in control.

Water can also be added to the wells 14 on a daily basis with the fluidics to maintain the required concentration of fluid on the cell. Liquid can be delivered into the well 14 by maintaining an environment above the well 14 at a slightly higher temperature (D), that will cause condensation in the well 14 (E) when needed to maintain the fluid level in a well 14. When the hotter, moister air settles down into the wells, the cooler temperature of the wells causes the moisture in the air to condense onto the walls of the wells. Since the plate sits on a heated, clear window, at 37 deg C., it is possible to lower the temperature of the window. Lowering the temperature of the window cools the liquid in the well. Since the well is at a temperature lower than the humid air, below the dew point, water vapor will condense in the well. This method allows for a procedure to compensate for loss in fluid due to slight or very slow evaporation in the Biobox. A fan (F) can be used over the heated water to control the % humidity (G), with a humidity sensor feedback. The fluidics, used to introduce and remove fluids from the Biobox and micro assay plate 16 well 14 currently includes a syringe (A) to pump liquids into and out of the Biobox and a valve (B) to direct the fluids to various vials (C) and paths to the cells. The valve, a standard series 1000 switching valve from Kloehn Company, Ltd., 1000 Banburry Cross Drive, Las Vegas, Nev. 89134, is switched to connect desired input path to desired output path.

The gel lid is a premolded piece of gellatin the size of the plate about 1/8 inch thick. This material is translucent to a light source above so light is dispersed in all directions as it enters the well. The gel can also slow down the diffusion of water vapor out of the well and a needle can enter the chamber through the gel.

The humidified environment for the cells also contains the control of carbon dioxide (CO2) content, typically controlled at 5% CO2 in air (79% nitrogen, 21% oxygen). The ambient CO2/air control can be further controlled to control oxygen levels, but controlling the precise mixing of CO2 and additional nitrogen into the humidified environment so as to reduce the level of oxygen. In this reduced oxygen environment, humidity still needs to be maintained at proper levels by us bone dry gases and adding the humidity supplemental as described herein.

The system has one needle (D) attached to the Biobox that is controlled by a controller of the apparatus and can add or remove fluids from individual wells 14 as well as to a station within the Biobox for cleaning the needle (E) and removing waste from the Biobox sterile environment. The needle is located over the well and a signal is sent to the controller of the needle to move to a position 0.094+/_0.002 inches from the bottom of the well. A signal is next sent to the syringe to draw out 30 microliters at a speed of 5 microliters/second. The needle is then moved to 0.023+/_0.002 inches from the bottom to touch the liquid then the needle is commanded to a position of 0.047+/_0.002 inches from the bottom. The syringe is then commanded to remove an additional volume until the meniscus breaks. That will leave about 4 microliters of liquid in the well. The rate of removal of liquid at this depth is 0.5 microliters/second.

The fluidics can be a fully automated process, for example to stain on demand such as when a cell divides. The fluidics can also be programmed to add or remove liquids from specific wells 14 of the micro assay plate 16 at a specified time, due to a cell event, such as division of the cell. The fluidics can also be used with operator intervention to add or remove a liquid to study the effect that a fluid has on cell motility or cell death. The fluid can contain a protein or some other typo of biological or chemical moiety. The fluidics system is able to stain adherent and non-adherent cells with minimal, or no cell motion, so that the cells can be imaged before and after staining and can be identified with both visible and fluorescence. This involves moving the needle (F) as close to the cells (G,H) as possible, dispense rates, capillary action and surface tension of the liquid (I) are all issues.

In the process of staining a cell, in a well 14, the solution above the cell is removed, as much as possible, and the rate of removal as well as how close the needle is to the cell is critical. A liquid is then added to the cell, for example a liquid with-an antibody with a fluorescent dye to link to a surface marker on the cell. The antibody stains can be purchased from PharMigen, 10975 Torreyana Rd., San Diego, Calif. 92121. A list of dye-antibody-cell relationships can be found in this company's catalog, incorporated by reference herein. The introduction of this antibody requires the needle to first come down close to the cell and touch the remaining liquid, then move up a specified distance pulling the liquid up by surface tension. The fluid is slowly dispensed so that the cell does not move. After the required incubation, the antibody links to the cell antigen. The remaining antibody solution in the well 14 must then be removed and replaced with a nonfluorescent solution.

For example, for detection of T lymphocyte differentiation from early lymphoid progenitor cells, a phycoerythrin fluorescent dye-conjugated anti-CD3 antibody may be used (Pharmingen Catalog 430105X). Similarly, for B-cell differentiation, a phycoerythrin-conjugated anti-CD19 antibody may be used (Pharmingen Catalog #30655X), or a mixture of both antibodies may be applied for detection of either B or T cells.

The movement of the needle with respect to the plate and the wells is controlled by predefined measurements that have been stored into the controller memory. The needle removes fluid from a desired well by first having the well chosen, either manually, or by a scheduler in the controller identifying that it is that well's turn next for review and processing. All the locations of the wells relative to a reference point of origin for the needle have been stored in the controller. As the needle moves from its origin point, the controller keeps track of the needle's location and can thus know exactly where the needle is relative to any given well in the plate at any time. When a given well is identified, the needle is moved over the well and then moved down a predetermined distance that has been previously measured. The fluid surface height in the well is also predefined to be essentially the same and at a given predefined height in all the wells from the preparation stage. If a well is to have a different fluid height for some reason, then this can also be stored in the controller.

The needle moves down the predefined distance that results in it penetrating through the surface of the liquid in the well. A pump, which creates a suction to withdraw the fluid, is activated for a predetermined period of time, causing a predefined amount of liquid to be removed, since the operation of the pump for a given period of time has also been calibrated and determined in regard to movement of fluid by it. After the pump has caused a suction in the needle, resulting in fluid being withdrawn from the well for a predetermined period of time, the pump is stopped. If the instructions for that well are such that more fluid needs to be withdrawn, then the needle is further moved down a predefined distance so it again penetrates through the now lower surface level of the fluid in the well. The pump is then reactivated and the fluid is withdrawn.

The operation of the needle whenever it needs to remove fluid in any well is repeated, as explained above. Similarly, the reverse can occur for the introduction of fluid into a well.

The needle is moved to a predetermined distance down to a given well. This causes the needle to penetrate the surface of the fluid in the well. Then, the controller causes the needle to move up a predefined distance that is known to pull the liquid up by surface tension with it and then stop without causing the liquid to break away and ruining the coupling. The desired fluid is then dispensed at a desired rate, which has been preprogrammed into the controller with respect to the operation of the pump.

Generally, if specific external actions are applied to the cell, such as staining, the well of the cell is caused to have a fluid at a very low viscosity. This low viscosity environment prevents the cell from being able to move very much and keeps the cell still in place. If the analysis of the cell requires the cell to be in a more viscous solution, the cell will be able to climb upwards or move around the well. In such an environment, the imaging of the well should occur first to insure that the cell is not in a region of the well in which, for instance, fluid will be extracted, and thus possibly injuring or killing the cell. The imaging step before the removal of fluid from a cell can be programmed for the given well, since the memory of the controller keeps track of the attributes (including cell location, morphology, motility, phenotypical markers, etc.) of each cell at any given time. The controller can cause the imaging of the cell first, such as with a focal stack, and the analysis of the well in regard to the region in which fluid will be introduced or removed from this well to ensure that the introduction or removal of fluid from the well will have minimal impact on the cell. By minimal impact, it is meant that after fluid dispensing or aspiration, that the controller still can recognize the cell(s) being analyzed by their attributes.

Furthermore, if a given well is to be processed more often than other wells, then a scheduler can keep track of all the wells, and each well can be given a weight with respect to its priority as to how often it should be analyzed. Then, a scheduling algorithm, for instance a weighted round robin can be used to process the different wells.

To get a clean background when taking a fluorescent image, the solution around the stained cell must be replaced 3 times, using the same procedure, again not moving the cell during the transfer of fluids. The same issues are involved when staining multiple cells, if cell position is required. This procedure can be used to detect which cells are live cells vs. dead (or versus a subpopulation of cells with a specific phenotypical differences as measured by a fluorescent marker of a morphology, motility or some other visible difference) and which cells have a specific surface 11 marker (antigen) or internal marker such as a nuclear stain. Staining is able to be performed with minimal background since most of the stain can be removed and the well 14 flushed multiple times, after the cells are stained. This permits the detection of very low thresholds of fluorescence from a cell with good repeatability. Staining occurs at 37C, body temperature. These stains are usually incubated at 4C, the incubation is shorter at 37C, but nonspecific staining is possible, so the incubation times must be shorter and more accurately controlled.

Cells can be separated after division, with recognition by the controller and aspiration by the fluidic pipettes, and placed in separate wells 14. One way to do this is to just mix the well 14 up and dispense ½ in 2 wells 14, another way is if the cells are separated, move a needle in and just aspirate out one of the cells (or a small subpopulation of the cells), then move it to another well 14 and dispense the cell/fluid. The needle is put in the view field of the microscope 18. The needle will have micron control of position and needle depth and the cell can be seen when the needle is present. The intent then is to have even better control of the fluidics with the help of the optics, for cell position. Another alternative is that the controller knows the x-y-z position of any specific cell(s) with the plate. The controller can direct the action of the pipette to go to a specific place in a well and aspirate the cell(s) at that location to put thin into another well or to pass them through the fluidics to a container outside of the biobox for further off-line analysis.

It is possible to move all the solution around a cell, in a specified well 14, out of the Biobox to a secondary plate 16, that can be placed in an incubator 24 off the instrument or analyzed say in an optical reader, mass spectrometer, etc., linked to the system. Many cells secrete proteins that indicate a specific cell function. The fluidics is able to remove the liquid above the cell, by the same procedure as staining, then pump the removed fluid to a vial (C), or plate 16 for analysis.

The fluidics on the apparatus can have more than one needle. One needle can be used to dispense buffer (J), or growth factors or antibody solutions. The second needle (K) can be used to remove fluids from the well 14. This speeds up the staining process. With one needle, the needle needs to move to a waste/cleaning station to dispense the fluid removed from a well 14. This is required a number of times during the staining process.

With 2 needles, this motion would be greatly reduced, since motion to the waste would not be required. The only motion that would be needed would be at the end of the staining process where the needles would need to be cleaned before entering another well 14 if contamination well 14 to well 14 is an issue. Multiple pipette tips can be used, especially in configurations of 8 pipette tips and 96 pipette tips. The density of the pipette tips has to be spaced depending upon the type of well plate used (6 wells to 9600+ wells).

The needle can have more than 1 tube. If there are for example 2 or 3 tubes in a needle (or pipette tip), one can be used for delivering while the second would be used for removal. This again would speed up any aspiration or dispensing process, since there would be no motion between needles or back to the cleaning station. The third tube in the needle would be used to deliver the expensive fluids; antibodies, growth media (L) etc. There would only be one motion at the end of the staining to clean the single needle (with multiple tubes). In order to improve the sensitivity of the stain, the stain is transferred to an unused well 14 (A).

The stain typically resides in a chilled vial until it is needed to stain a cell. The needle then is used to pipette a small volume of stain into the well 14, with greater accuracy. The dispense into the well 14 with the cell, is more accurate, (do not have to dispense a greater volume down the tubing), to be assured that the antibody is actually in the well 14, and there is no introduction of bubbles into the well 14. Bubbles cause motion of cells. At first, a well/cell was stained at the time of division; this process takes about 15 to 20 minutes, with a single needle. During that time little else can be done, some multiprocessing is possible. If a second cell divides during this process, it cannot immediately be stained.

As the number of wells in an experiment climbs from 50 to 100 wells, up to 300 to 500 wells and higher, it will not be possible to track cells, process and stain cells in each well, one at a time without an increase in computing power. Batch staining each cell will be tracked and division detected, the divided cells will go into a list of cells to be stained. At a specific time, say the morning, all the cells will be stained. The batch staining will be much faster, since first the liquid from all the wells 14 is removed, then the antibody is added to each well 14, until all wells have antibody added, etc. This will permit higher volumes of cells to be moved through the instrument. When the cells divide, it may be necessary to remove the growth factor and add a quiescent media before the cells are stained. A description of the process and the specific growth factors can be found in "Influence of Cytokines on the Growth Kinetics and Immunophenotype of Daughter Cells Resulting From the First Division of Single CD34+Thy__+lin__Cells" by Julie P. Goff, Donna S. Shields, and Joel S. Greenberger; Blood, Vol 92, No 11 (December 1), 1998: 4098–4107; The American Society of Hematology, incorporated by reference herein. A quiescent media is a solution that stops or slows the cell function. There are many possible quiescent media, if the cells are being tested in serum free media with specific growth factors, a quiescent media may be the serum free media with a lower concentration of the growth factors, such as 1%, The solution around the cell is removed and the quiescent media is added. If for example the surface marker after division is short lived, and the needle cannot reach the cell to stain it, if the solution is in the quiescent media, the marker will remain on the cell surface longer and then can be stained as part of the batch staining.

The other approach is to kill the cell and look at the cell surface markers at the time of doubling. This can be accomplished by again removing the growth factor solution and fixing the cell, with a solution, stopping any cell function, then staining when possible. A low concentration of ethanol or a formalin solution will fix a cell for later staining in the batch procedure.

When staining cells in an experiment, it is necessary to have both positive and negative reference cells that are stained to verify the sensitivity of the stains to the antigens being detected. There are wells 14 where there are cells that have known sensitivity to the stains, in the same environment that will also be stained to verify the detection is working properly. Beads 20 can be added to the wells 14 that produce fluorescence to a known intensity, this verifies the sensitivity of the optics during the experiment.

The present invention pertains to a method for determining a condition of a cell. The method comprises the steps of placing a bead 20 coated with a first material in a well 14 of a plate 16. There is the step of identifying a second material released by a cell in the well 14 by the second material reacting with the first material.

Preferably, the identifying step includes the step of staining the bead 20 with a stain that identifies when the second material reacts with the first material. There is the step of coating the bead 20 with the first material.

Figure 8:
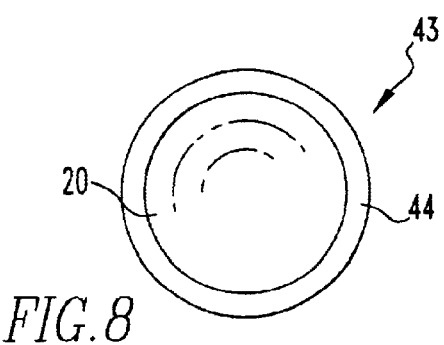
FIG. 8 is a schematic representation of an apparatus for indicating a condition of a cell.

The present invention pertains to an apparatus 42 for indicating a condition of a cell, as shown in FIG. 8. The apparatus 42 comprises a bead 20. The apparatus 42 comprises a layer 44 of a first material which reacts with a second material which is released from the cell when it is in the condition. The layer 44 coats the bead 20.

It is possible with the system to add beads 20 to the wells 14 that have cells. These beads 20 would be coated with an antibody that would bind to specific secretions from a cell, such as proteins. Many beads are introduced into the environment, and as the cells secrete specific proteins, based on the growth factors in the solution, the antibody on the beads would bind to the protein secreted from the cell. Under conditions such as known growth factors, the beads 20, once stained would identify the presence of the secretion. The beads could be stained in place and the proximity of the bead to the cell would indicate which cells are secreting the protein of interest.

Soluble proteins secreted from cells of interest could include cytokines such as IL__4, IL__8, gamma-interferon, and others. The antibodies against these proteins may be obtained in pairs such that the capture antibody and the detection antibody both bind to the target cytokine or other molecule without interfering with each other. The capture antibody is bound to the bead prior to addition to the cell culture well. The detection antibody is labeled with a fluorescent dye such as phycoerythrin, and is added to the well after sufficient time has elapsed for the capture antibody to accumulate cytokine proteins secreted from the cells. Beads with different features (e.g. size, shape), could be used with different antibodies and with different fluorescent dyes to detect multiple soluble proteins simultaneously. Antibody pairs directed against IL__4, IL__8, and gamma-interferon are available from Pharmingen (Catalog #'s 2629KK, 2654KK, and 2613KK, respectively) See the catalog from this company, incorporated by reference herein. Capture antibodies may be bound to the beads by various methods including direct adsorption, covalent attachment, and attachment through a generic binding protein such as Protein A. Depending on the antibodies, the culture conditions, and procedures used, one or more of these methods would be optimized for maximal effectiveness. Details of these methods are presented in technical notes from Bangs Laboratories, Inc, 9025 Technology Drive, Fishers, Ind. 46038-2886, specifically TechNote #204, Adsorption to Microspheres (direct adsorption), TechNote #205 Covalent Coupling (covalent attachment), and TechNote #101 Proactive Microspheres (Protein A mediated binding), all of which are incorporated by reference herein. These documents are also available on the internet at www.bangslabs.com/support/index.php.

The present invention pertains to an apparatus 28 for aligning light in a well 14 of a plate 16 for holding cells, as shown in FIGS. 7a–7d. The apparatus 28 comprises a top portion 30 that is adapted to hold to the plate 16. The apparatus 28 comprises a bottom portion 32 connected to the top portion 30 that is adapted to extend into the well 14 below a meniscus 36 in the well 14. The top and bottom portions are made of a transparent material which lets light pass through it and be distributed evenly throughout the bottom of the well 14.

Preferably, the top and bottom portion has a channel 38 extending through them for a needle to pass through the channel 38 and access the bottom of the well 14. The apparatus 28 preferably includes at least a second portion 40 extending from the top portion 30 and adapted to be disposed in a second well 14 of the plate 16.

The present invention pertains to a method for lighting a well 14. The method comprises the steps of placing a top portion 30 of a light alignment apparatus 28 onto a plate 16 having wells 14 so a bottom portion 32 of the light alignment apparatus 28 extends into a well 14 and below a meniscus 36 in the well 14. There is the step of directing light onto the top portion 30 which is evenly distributed by the bottom portion 32 to the bottom of the well 14.

Figure 7A:
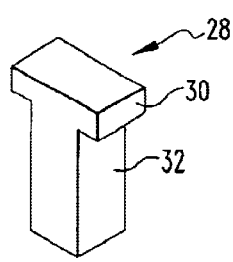
FIGS. 7a–7d are schematic representations of an apparatus for aligning light in a well of a plate for holding cells of the present invention.
Figure 7C:
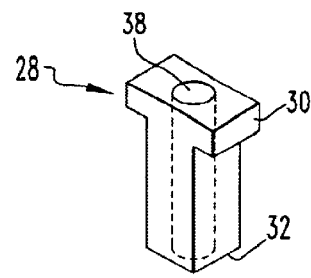
Figure 7B:
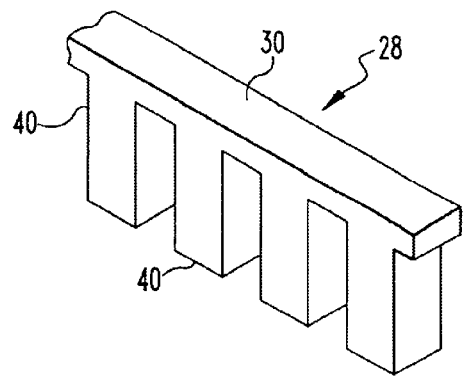
Figure 7D:
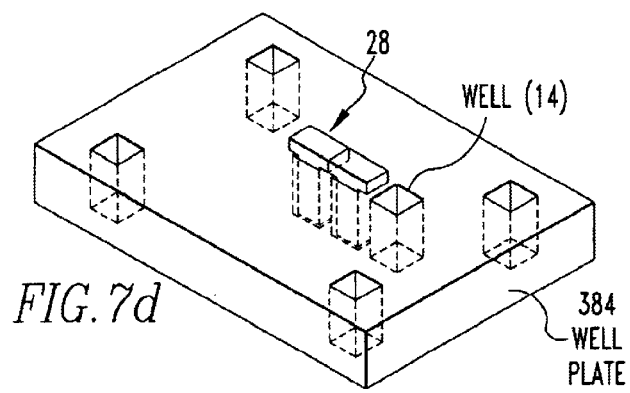
Figure 7E:
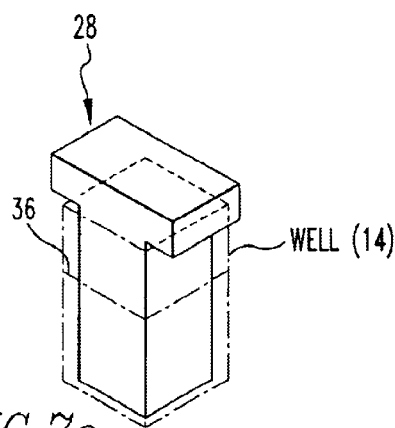
Figure 7F:
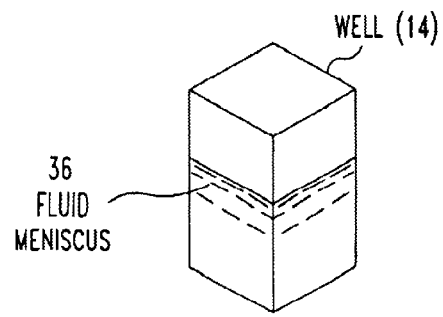

There are many possible ways to illuminate the cells, visible light from above (or below) collimated, phase contrast light, fluorescent light and laser light. Fiber optic light, possibly more than 1 light can be used. Better contrast can be achieved for the cell image, by reducing the effect of the meniscus of the well 14 fluid level. The needle may also be in the view field so 2 to 3 fiber lights (A) (B) may be required. One of the difficulties when lighting a well from above is the refraction of light as it enters the meniscus of the liquid in the well. The meniscus acts like a lens, changing the lighting pattern on the cells below. In small wells such as 384 well plates, the center of the well is much brighter than the edges of the plate. Phase contrast, a preferred method for viewing live cells, is distorted, since the light is no longer collimated. In the center of larger wells, such as 96 well plates, collimated light, needed for phase contrast, can be obtained in the center ⅔ of the well. In 384 well plates, only a very small region in the middle of the well is acceptable. FIGS. 7a–7d show a light alignment apparatus 28. FIG. 7a is an optically clear material such as plexiglass or glass that is dimensioned so that it fits down inside of the well 14. The apparatus 28 is long enough to break the meniscus 36 of the liquid in the well 14. The collimated light from above strikes the clear alignment apparatus 28 and passes straight through to the liquid below. The meniscus 36 no longer distorts the direction of the light. Phase contrast images can be obtained for a large portion of the well 14. The apparatus can be manufactured for individual wells (FIG. 7*a*), or a series of 10 or more can be produced (FIG. 7*b*). It is possible to manufacture one alignment apparatus 28 for the full 384 well plate. This embodiment works best for phase contrast images if the top and bottom surfaces are flat, so as not to distort the collimated light. The second portion 40 that fits into the well, can not go completely to the edge of the well 14, since a small area is needed for fluid exchange with the environment above. A variation on this embodiment (FIG. 7*c*) is a light alignment apparatus with a channel 38 in the middle. This breaks up the meniscus 36 but allows for a needle to also enter the well 14. In this variation however, more uniform lighting can be achieved on the bottom of the well, although not phase contrast light. Directing the lighting to this apparatus 28, channels the light to the bottom of the well, producing a reproducible condition, independent of the height of the liquid or the presence of a needle into the hole in the center.

Figure 9A:
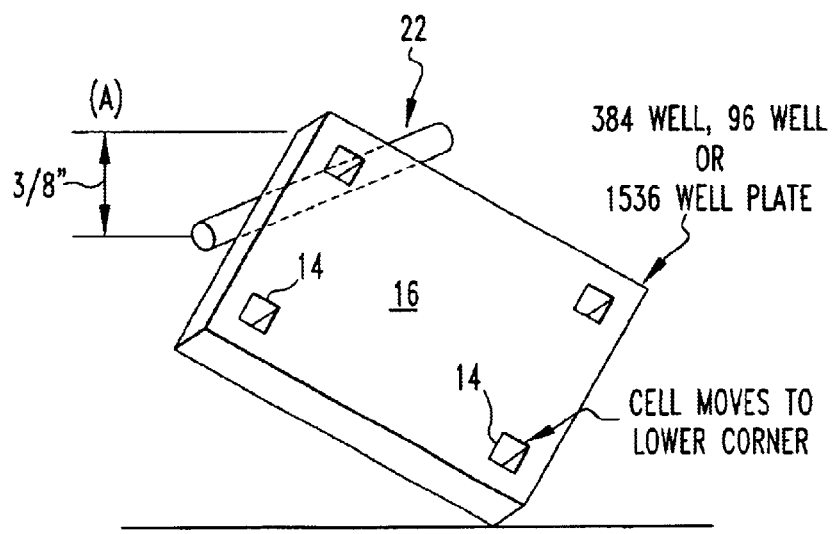
FIG. 9a is a schematic representation of a well plate that is tilted.

FIG. 9*a* shows a 384 well 14 plate 16. This plate 16 is 5 inches×3.37 inches×0.56 inches thick. This is a molded plate 16 that is sterile and holds the cells. The plates 16 can be 6 wells, 12, 24, 96, 384 or 1536, or higher densities up to 9600 wells or greater. They can be glass, quartz, clear plastic or white or black plastic sides with clear plastic or glass bottoms. The operators take this plate 16 into a hood and plate 16 the cells, (they pipette cells into the wells 14) or a liquid handling robot can be used. The cells can be transfected or transduced with cDNA libraries or protein libraries before plating. Various fluids that the cells need; serum, and or proteins of interest can also be added by the user or through fluidics. The cells fall to the bottom of the plate 16 over a number of minutes/hours. This sketch shows a first embodiment, where the plate 16 is tilted with a pencil on one corner. The plates 16, and pencil, are placed in an incubator 24 for a day. The cells fall to the bottom and move to the lower corner of each well 14. The operator then knows to look in the lower right hand corner to find a cell or cells if interest. These cells are very small 10 micro meters in diameter in a large area. This simplifies the locating of single cells in the wells 14.

Figure 9B:
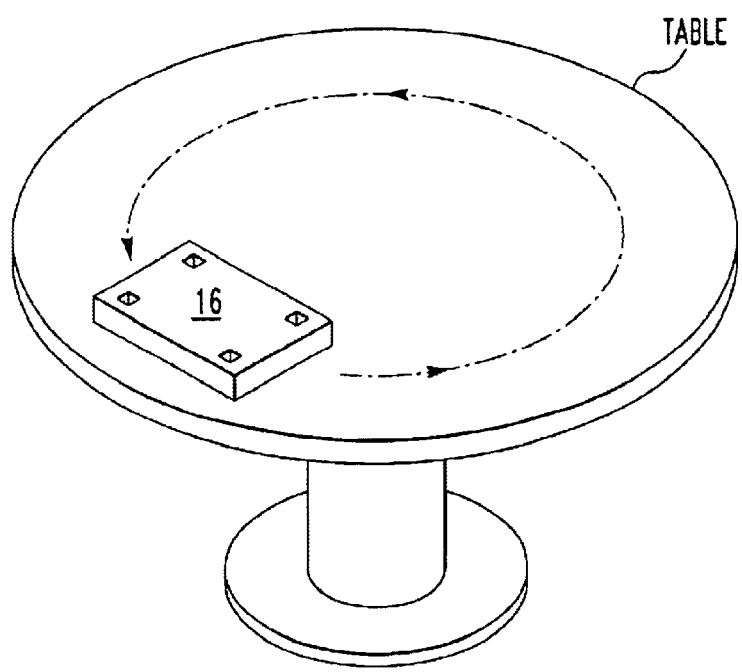
FIG. 9b is a schematic representation of a horizontal centrifuge for a well plate.

FIG. 9*b* shows a horizontal centrifuge. There is a motor at the center and a flat disk that spins. The same plate 16 as described above is placed on the table and secured. The plate 16 is then spun, with the plate 16 first set so that the corner of the well 14 is toward the outer edge. The range of rotational speed is experimentally determined, dependent on the amount of liquid and it's density. For low viscosity liquids such as a buffered solution, with a 384 well plate filled with 30 microliters, (about ⅓ full), the table is spun to a speed where the liquid just leaves the wells. Then a speed 10 to 20% below that level is used when the cells are present. The RPM is approximately 200 to 300 RPM. If larger volumes are required, the RPM level is reduced, if a more viscous solutions are used, such as methyl cellulose, then the RPM level can be increased. As the plate 16 spins, the cells, since they are more dense than the fluid, are spun to the outside corner of each well 14. The 384 well 14 plate 16 along with the apparatus 10 are placed in an incubator 24 and spun over night to again get the single cell to the outside corner of each well 14.

Figure 9C:
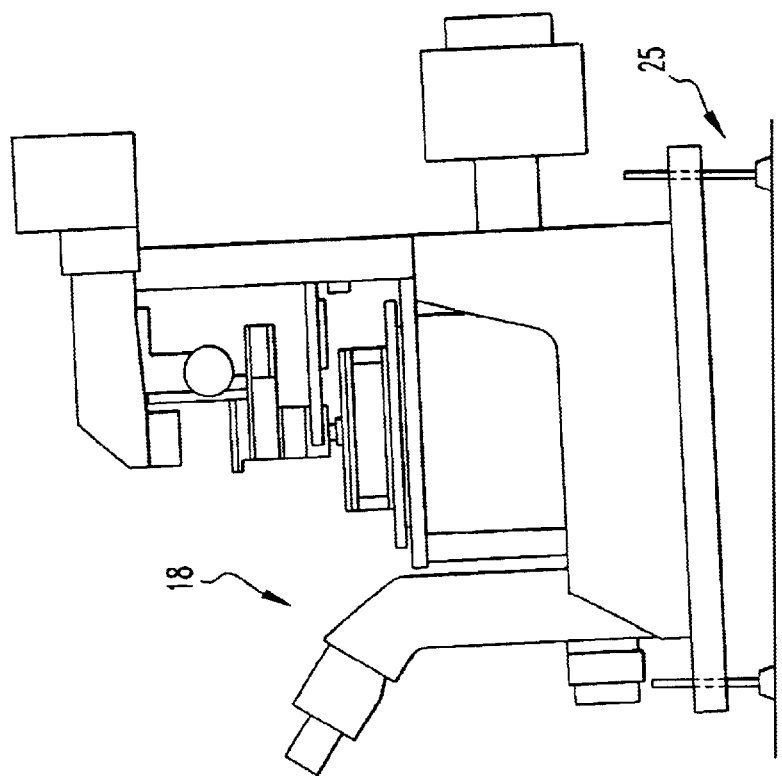
FIG. 9c is a schematic representation of a side view of a microscope that is tilted.
Figure 9D:
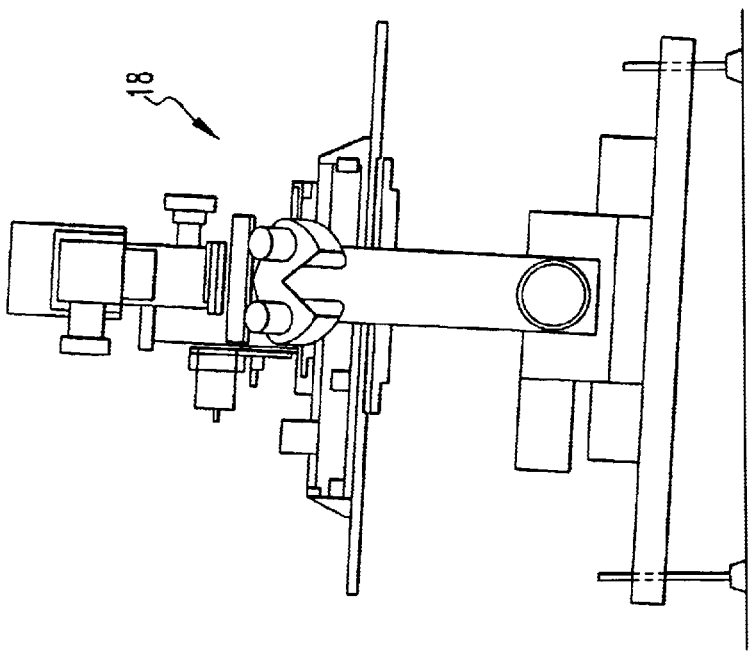
FIG. 9d is a schematic representation of a front view of a microscope that is tilted.

FIG. 9*c* and FIG. 9*d* shows another method to cause cells to move to the corner of a well 14. In this case, a piece of ¾ plywood, or similar material, is placed under the microscope 18 and the complete apparatus 10 is tilted. At the corners of the plywood there are threaded posts that are manually adjustable. The operator can adjust the angle by turning the posts to a desired direction and angle. In the 2 methods described above (1 a and 1 b), most of the cells move to the corners, but some of the cells still do not get to the corner. It is also possible for there to be more than 1 cell in a well 14, and one of the cells moves faster than the other. In any case, when the plate 16 is mounted in the instrument, there are wells 14 where the cell isn't in the lower right hand corner. If the whole device is tilted, the cells move or stay in the lower right hand corner. So it is possible to keep cells in the corner of a plate 16 as well as to locate cells that take longer than say a day to move to the corner. It is also now possible to think about an automatic way to locate these cells. The process of finding cells is very tedious, and finding an automated way of locating the cells is very desirable. It would also be possible to tilt the plate 16 in the apparatus 10, instead of tilting the whole device. The issue here is that the focus would then change so you would have to refocus if you made a change in the tilt of the plate 16.

Figure 1A:
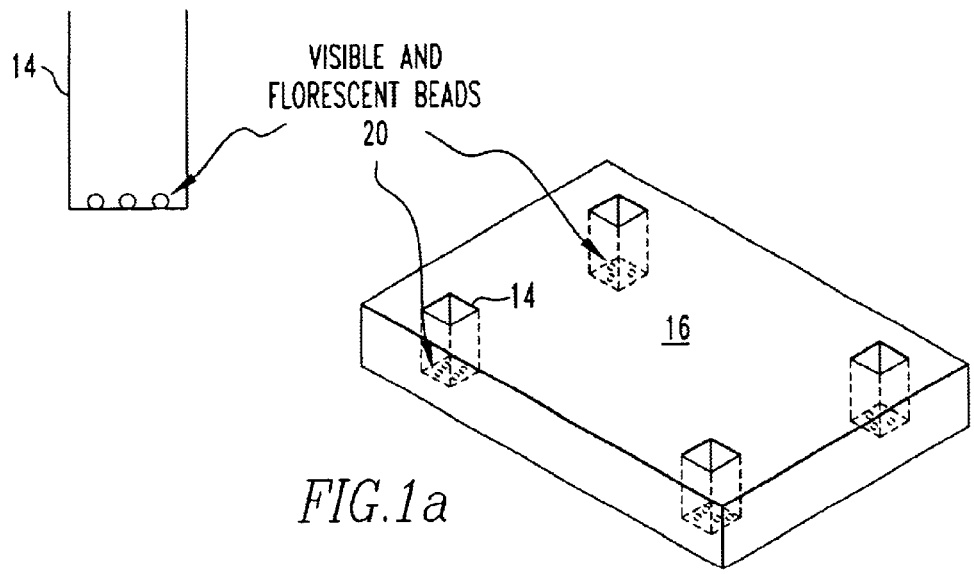
FIG. 1a is a schematic representation of a plate with beads in a well.

FIG. 1*a* shows a 384 well plate 16. In certain wells 14 in the plate 16, beads 20 have been added to the well 14. The beads 20 are about 2 micro meters in diameter, although you can get various diameter beads 20 are available. The beads 20 are fluorescent. It is possible to drop beads 20 in a well 14, they will drop to the bottom of the well 14. The focus on these beads 20 is simpler, easy to find. These beads 20 are also fluorescent, so the microscope 18 can be configured to look at fluorescent samples, in this case beads 20. The focal sensitivity for fluorescence is much more exact than the focus in visible. Focus is performed on 3 or more parts of a plate 16 and have the instrument then focus on the rest of the plate 16 based on that 3 point position. The instrument can then move to any position in the plate 16 and the focus is determined based on this 3 (or more) points in the plate 16.

Figure 1B:
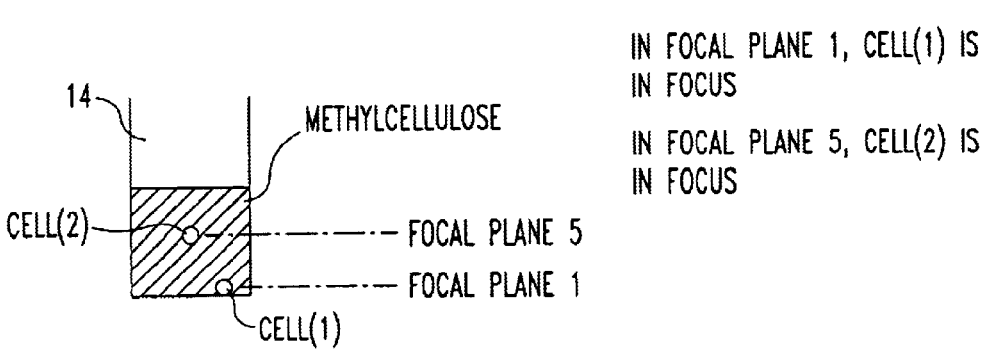
FIG. 1b is a schematic representation of a well and a microscope objective.
Figure 1B:
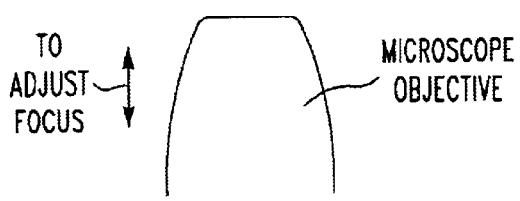

FIG. 1*b* shows a single well 14 in a plate 16. In this case methylcellulose is added to the well 14. Since methylcellulose is more dense than regular serum, the cells are able to move into a third dimension, if the viscosity is high enough. A stepper motor is attached to the focus knob of the microscope 18 and images can be taken at any plane in the well 14. If a cell is in focus, the edge of the cell is sharp or well 14 defined. Cells that are on the bottom of the plate 16 are well 14 defined if in focus. If the cells are in methyl cellulose, many will climb to a higher plane. The system takes images at various planes and it is possible to locate planes where the cells are in focus. Cells can be tracked not only in the x-y plane, but also in the z or vertical plane.

Figure 2A:
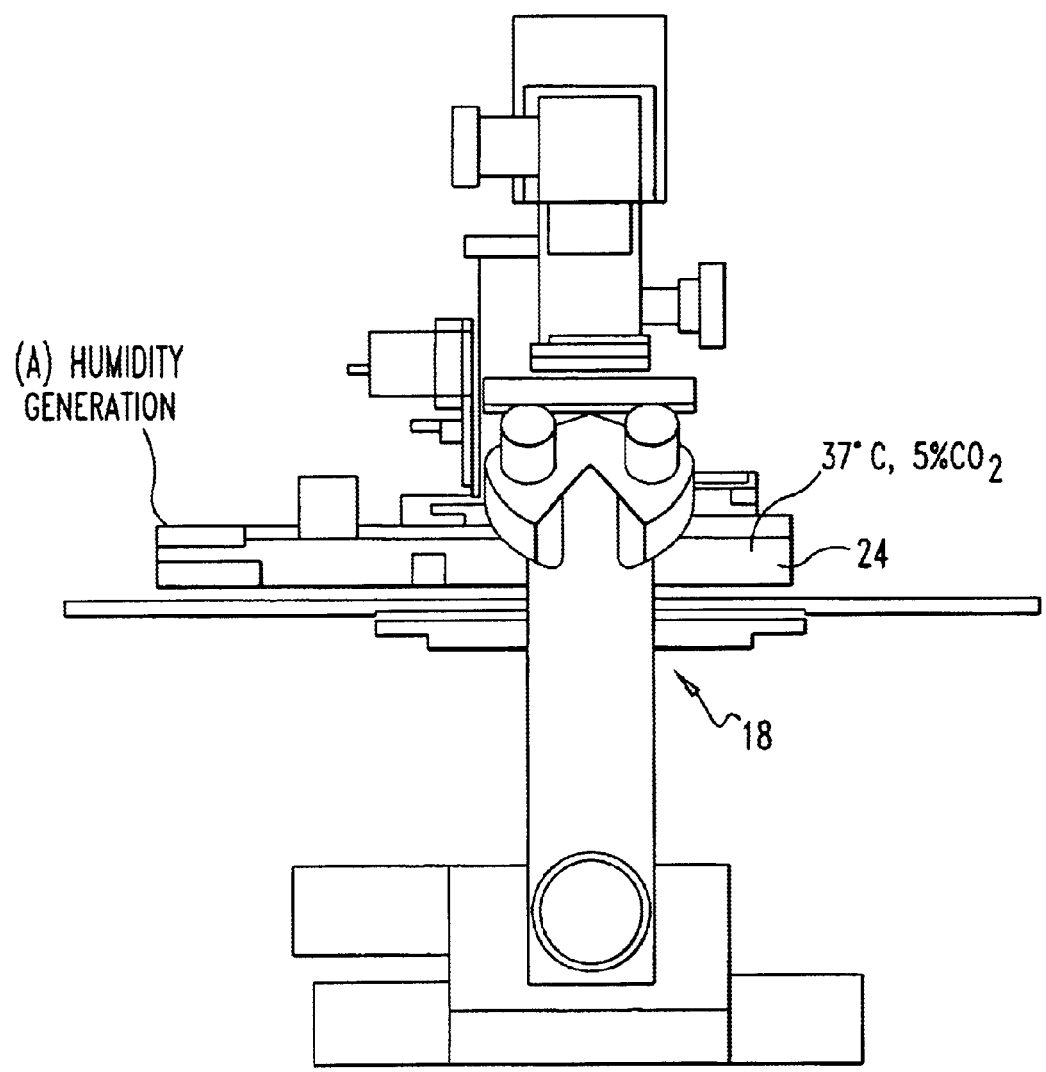
FIG. 2a is a schematic representation of a microscope with a biobox having humidity above generator.

FIG. 2*a* shows a humidity generator that was added to the Biobox on the instrument with a separate heater. The heater has a temperature feedback, so by adjusting the temperature of the bath, water can be pumped into the box. This temperature, usually around 50 to 55C, will keep the water in the wells 14 from evaporating.

Figure 2B:
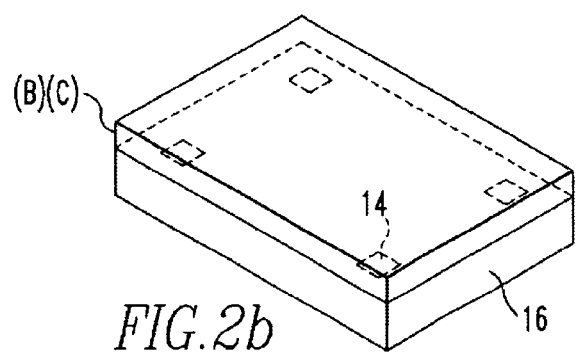
FIG. 2b is a schematic representation of a well plate having a piece of paper over the top of the wells.

FIG. 2*b* shows a 384 well plate 16, that has a piece of sterile paper over the top of the wells 14. The paper is porous and can be wet, to help control evaporation out of the wells 14. The plate 16 usually has a plastic cover on it. This cover will fog up if there is condensation from above the cover or below. If the cover is removed, the wells 14 will dry out more quickly. Filter paper is added so that air movement in the box will not cause evaporation out of the wells 14. The other problem with condensation on the lid is lighting. When looking at cells in the bottom of these wells 14, the lighting is introduced from above the plate 16. If there is condensation on the lid, large dark spots appear in the viewfield. By removing the lid and using paper, the light is diffused and better lighting is achieved, easier to see the cells. This cover can also be made out of other materials, such as a gel.

Figure 2C:
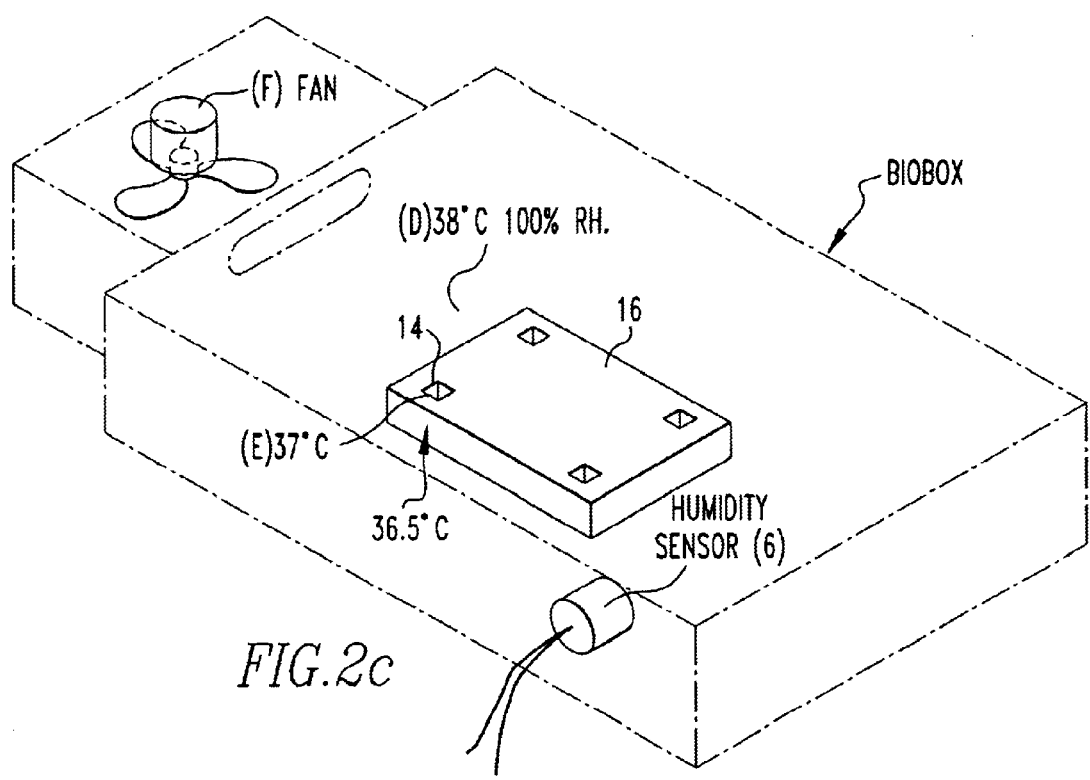
FIG. 2c is a schematic representation of a fan over top of a heated water bath.

FIG. 2c shows a fan over top of the heated water bath. When the fan is running, the amount of evaporation from the bath is increased, therefore increasing the relative humidity in the box. There is a heated window on the under side of the plate 16. Since the temperature in the wells 14 of the plate 16 is controlled, it is possible to lower the temperature in the wells 14. If the temperature in the wells 14 is lowered, it is possible to cause water to condense in the wells 14, keeping the fluid level from evaporating.

FIG. 3a shows components which make up the fluidics on the system. The syringe and valve are both controlled by stepper motors. The modules communicate via serial communication. The needle drive is mounted on the Bbiobox and controls the up/down motion of the needle, again with a stepper motor. By moving the table, the needle can be located over a given well 14, then commanded to move down into the well 14. The system can accurately add or remove fluids from any well 14 or move fluids into or out of the biobox. There is also a cleaning station inside the biobox. This cleaning station is necessary if there is possible cross contamination between wells 14. There is a pump connected to the cleaning station to remove waste from the station.

Figure 3B:
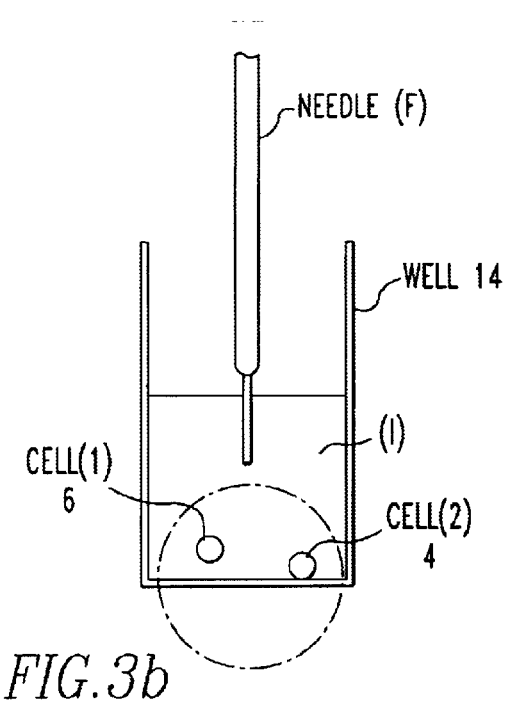
FIG. 3b is a schematic representation of a needle positioned over a well of a plate.

FIG. 3b shows a single well 14 in a plate 16. The needle (F) is positioned over the well 14 and lowered into a position in the center of the well 14. The needle is accurately positioned above the cells in the well 14 and the fluids added then removed to stain the cells. Cells that have minimal attachment to the bottom of the well 14 are called non-adherent cells. The cells can easily be washed or moved by the fluidics. Capillary action is also a strong factor in moving these cells. FIG. 5a shows 2 cells in the bottom of the well 14. By trying to stain those cells with minimal movement, it can be possible to identify which cell shows positive or negative to the stains.

Figure 3C:
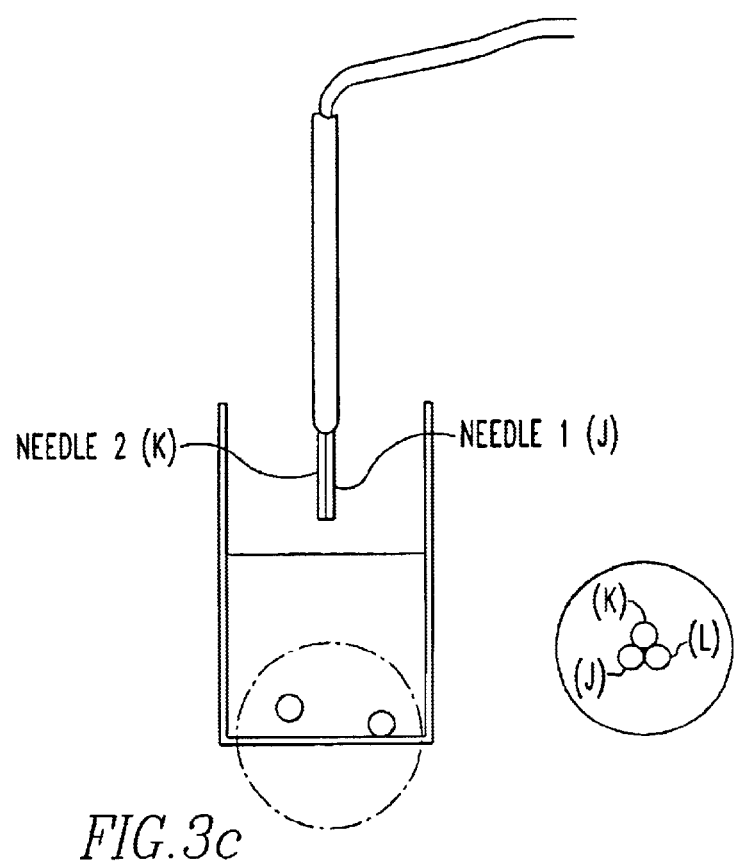
FIG. 3c is a schematic representation of a dual needle positioned over a well of a plate.

FIG. 3c shows a dual needle having 2 or 3 separate tubes that form a single needle assembly. If a single needle is used, the needle has to be moved to a cleaning station to get rid of the fluids removed from the well 14 and to a separate position to get fluids that are to be added to the well 14. With 2 or 3 tubes, each port has a function. One for removing waste, one for expensive antibodies and one for a flush fluid.

Figure 4:
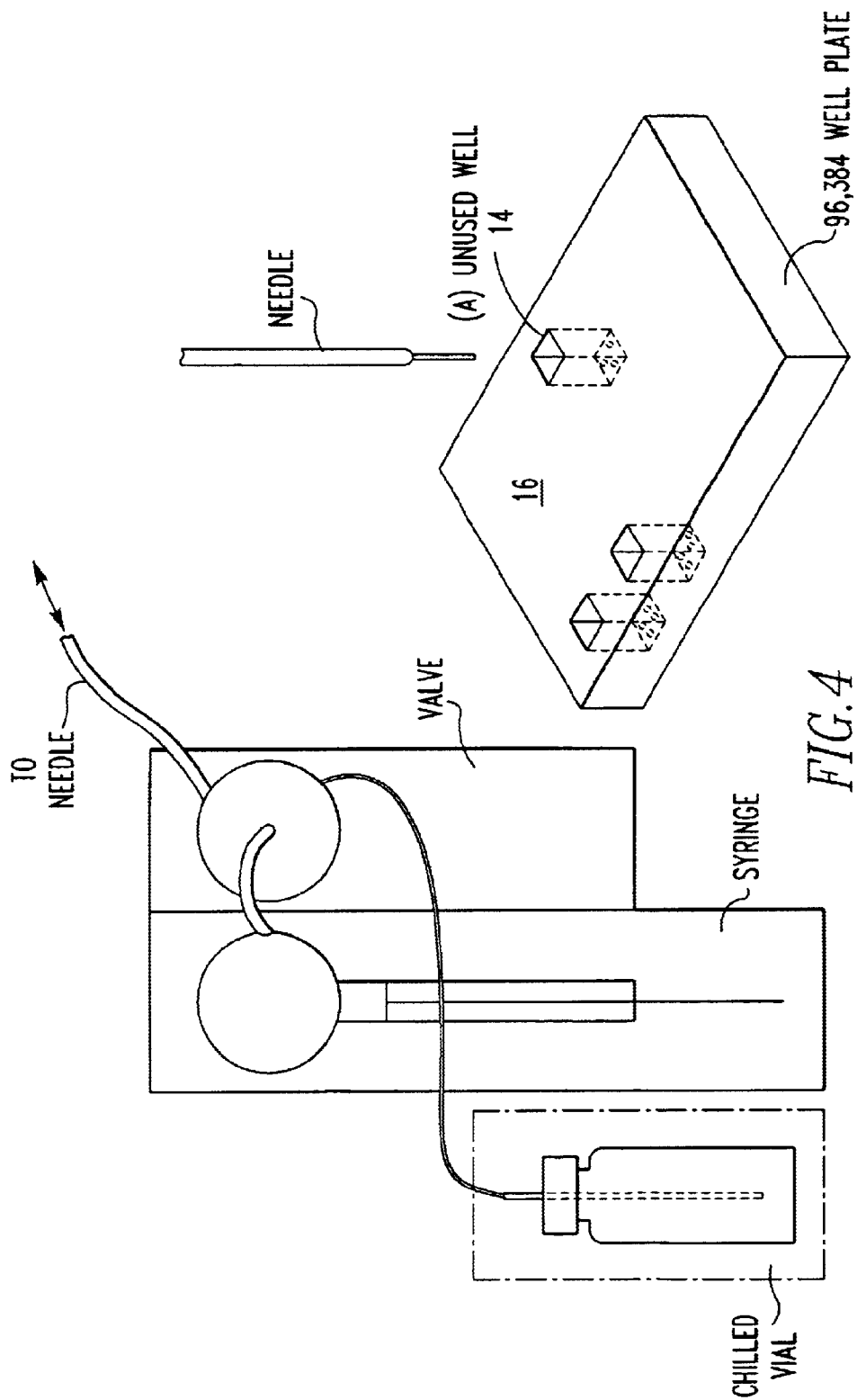
FIG. 4 is a schematic representation of the fluidics with a chilled vial connected to a needle over a well of a plate.

FIG. 4 shows the fluidics and a chilled vial. This vial holds the expensive antibody solution. The solution is usually kept at 4 deg C. until needed. At that point, the fluidics would move the stain to an unused well 14 in the plate 16, or to a well 14 just to the side of the plate 16. The volume is much larger, since a number of wells 14 are going to be stained.

Figure 5:
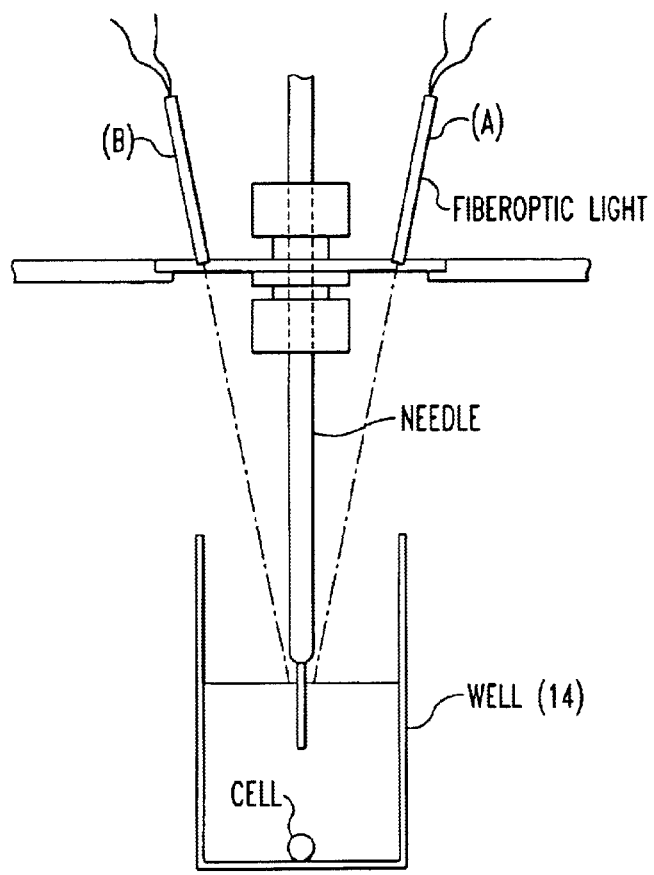
FIG. 5 is a schematic representation of a side view of the biobox with a needle aligned with the microscope objective.

FIG. 5 shows a side view of the biobox, with a needle aligned with the objective. Normally, cells are stained but they are not in the view field. FIG. 5 shows an embodiment for moving the needle in the view field by lighting the well 14 with lights around the needle. In the typical configuration of the instrument, the light path to illuminate the cells is from above the cells, with the objective below. The cells are illuminated with phase contrast light or direct collimated light. In order to introduce fluids into a well, the well is moved under a needle D, FIG. 3a, that is not located in line with the objective. When fluids are exchanged for staining, or samples added to the well, or removed, the well cannot be observed. In order to determine if cells have moved in the well, due to fluid exchange, a digital image is taken before and after the fluid exchange. The operator views the images to determine if the needle is too close to the cells or the fluid rate is too fast. This process for developing a fluidics procedure is time consuming. A new approach is defined in FIG. 5. In this case, the needle assembly is moved so that the needle is in line with the objective below. This configuration however blocks the lighting from above. In order to light the cells, light is introduced along the side of the needle. Since the needle is smaller, one solution is to have 1, 2, or 3+fiberoptic lights directed around the needle down into the well. This method allows the needle to be observed during the fluid transfer into or out of the well. Since cells can be observed during the exchange, reduced development times are possible. If smaller needles are incorporated, it is possible to move very close to a specific target, a cell, and deposit a protein (fluid) very close to a cell. It is also possible to select, or remove a cell from a well and deposit that cell in a specific place in another well. The addition or removal of a cell from a well requires very accurate location of the needle, fine control of the fluidics and the optics (needle over the objective), to be able to accomplish this task.

The present invention pertains to a method for manipulating cells. The method comprises the steps of guiding a pipette with a controller to a predefined position in a well of a plate having a predetermined cell. There is the step of aspirating the cell with the pipette from the well. There is the step of placing the cell at another location with the pipette at the guidance of the controller.

Preferably, the placing step includes the step of placing the cell in another well of the plate. Alternatively, the placing step includes the step of placing the cell in a container disposed outside the plate or delivering such cell(s) to an off-line device such as an ELISA reader or mass spectrometer.

U.S. Pat. No. 6,008,010, incorporated by reference herein, describes a system that can also be used to perform the embodiments described herein and U.S. patent application Ser. No. 09/904,144, incorporated by reference herein, describes the suppression of non-biological motion of cells in wells.

Figure 6:
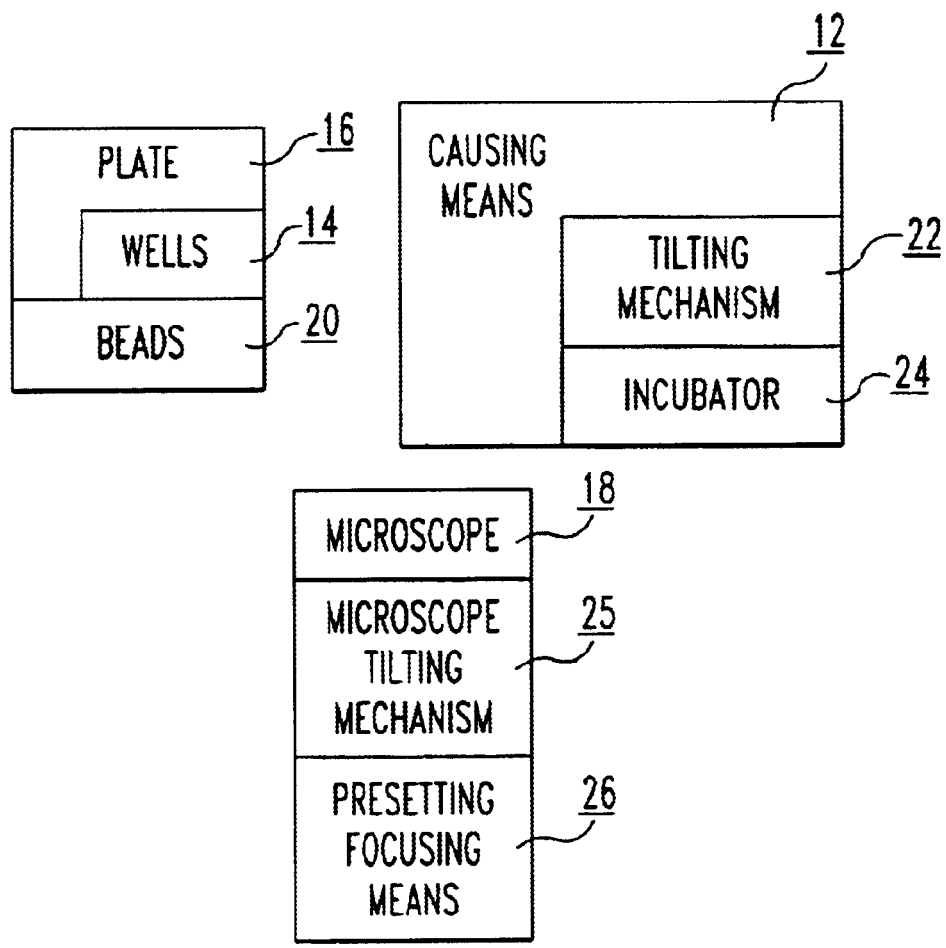
FIG. 6 is a schematic representation of an apparatus of the present invention.

The present invention pertains to an apparatus 10 for monitoring cells, as shown in FIG. 6. The apparatus 10 comprises a plate 16 having wells 14 in which cells are disposed. The apparatus 10 comprises means for causing each cell or population of cells to move to a corner of each well 14. The causing means 12 is connected to the plate 16.

Preferably, the causing means 12 includes a tilting mechanism 22 for tilting the plate 16. Alternatively, the causing means 12 includes a horizontal centrifuge inside an incubator 24, which spins the plate 16. The plate 16 is in contact with the incubator 24.

Preferably, the apparatus 10 includes a microscope 18, which locates each cell in each well 14. The microscope can have either visible or fluorescent or dual visible and fluorescent detection. Other forms of optical detection, such as confocal or DIC can also be used. The apparatus 10 preferably includes a microscope tilting mechanism 25, which tilts the microscope 18. Preferably, the apparatus 10 includes means 26 for presetting focus of the microscope 18 to the corner of each well 14. Preferably, the apparatus 10 includes beads 20 disposed in the wells 14 upon which the microscope 18 focuses.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

-39-

APPENDIX

Table 1

| Measured Parameter | Type of Parameter | Description |
|---|---|---|
| 1. Colony count | Proliferation, apoptosis | The number of objects in an image, where each object is a single cell or a group of cells. |
| 2. Object count | Proliferation, apoptosis | The number of individual cells in an image, determined by dividing each object area (parameter 1) by a user defined average area for a cell. |
| 3. Proliferation count | Proliferation, apoptosis | The number of cells in a view field, determined by first determining the average of all objects within 3 times the preset individual cell size. Then dividing each colony object by that average area to get a total cell count. |
| 4. Vinst(abs) | Motility | The average velocity of the instantaneous speeds, based on a specified number of images before and after the specific image. |
| 5. Vinst(angle) | Motility | The angle of the average velocity of the instantaneous speed, #4. |
| 6. Vinst | Motility | The instantaneous speed of the object. |
| 7. Vavg_inst(abs) | Motility | The instantaneous speed of the average smoothed track through a specified number of images before and after the specific image. |
| 8. Vavg_inst(angle) | Motility | The angle of the instantaneous speed, #7. |
| 9. Vavg_inst | Motility | The average of a specified number of images of the smoothed track at a specific time / image. |
| 10. Vsl(abs) | Motility | The straight line velocity of the average smoothed track. |
| 11. Vsl(angle) | Motility | The angle of the straight line velocity, #10. |
| 12. Vsl | Motility | The straight line velocity of the instantaneous speeds of the track. |
| 13. Vcl | Motility | The change in the average velocity over the full track up to a specific field. |
| 14. Vavg | Motility | The change in the average velocity of the smoothed track to a specific field. |
| 15. Linearity | Motility | The straightness of a cells motion, Vsl/Vcl. |
| 16. Straightness | Motility | The same as linearity, using the smoothed track, Vsl/Vavg. |
| 17. ALHmean | Motility | The measure of the oscillating amplitude of an objects motion. The average amplitude of the track oscillations around the smoothed track. |
| 18. ALHmax | Motility | The maximum amplitude of the oscillating component of the cells motion around a smoothed track. |
| 19. BCF | Motility | The average number of oscillations about the average track. |
| 20. Circular radius | Morphology | A measure of the circular component of the objects motion. |
| 21. Filtered objects | Proliferation, apoptosis | The number of objects that are filtered from the analysis, based on their individual speed. |
| 22. % motile | Motility | The percentage of objects that are more motile than a given area per image. |

-41-

| | | | |
|---|---|---|---|
| | 23. Elongation (avg) | Morphology | The ratio of the length to the width of an object. |
| | 24. Unique Track Index | Cell-specific Delimiter-Motility | The path of an objects motion over a specified number of images. |
| | 25. Track Size | Cell-specific Delimiter-Motility | The length of a track, or number of images that a cell was tracked. |
| 5 | 26. Track Boundary (pixels) | Cell-specific Delimiter-Motility | The region in pixels, or microns that bound the motion of the cell. |
| | 27. Start image | Experimental | The first image where a specific object was tracked. |
| | 28. End image | Experimental | The final image that an image was tracked. |
| | 29. Cyte | Morphology | The specified location in a plate that the object was tracked. |
| | 30. Avg Area | Morphology | The number of pixels / microns in an object detected. |
| 10 | 31. Min Area | Morphology | The minimum number of pixels or microns of an object in a track or time series. |
| | 32. Max Area | Morphology | The maximum number of pixels or microns of an object on a track or time series. |
| | 33. Mean intensity | Morphology | The average intensity of the pixels within an object. |
| | 34. Intensity Sum | Morphology | The addition of all the pixel intensities within an object. |
| | 35. Object Pixel SD | Morphology | The standard deviation of the intensity of all the pixels within an object. |
| 15 | 36. Area | Morphology | The number of pixels in an object. |
| | 37. X coord | Motility | The x coordinate of the center of an object in an image. |
| | 38. Y coord | Motility | The y coordinate of the center of an object in an image. |
| | 39. Perimeter | Morphology | The sum of the pixels around the perimeter of an object. |
| | 40. Fmax Diameter | Morphology | The maximum width of an object after the angle is swept by a specified preset angle. |
| 20 | 41. Fmin Diameter | Morphology | The minimum width of an object after the angle is swept by a specified preset angle. |
| | 42. Length | Morphology | The maximum width of an object. |
| | 43. Breath | Morphology | The minimum width of an object. |
| | 44. Elongation(L/B) | Morphology | The length / breath. |
| | 45. Convex Perimeter | Morphology | The approximation of a convex hull of an object based on a swept angle. |
| 25 | 46. Compactness | Morphology | The roundness od an object, perimeter squared / (4 pi Area). |
| | 47. Roughness | Morphology | Measure of the irregularity of the perimeter. Perimeter/convex perimeter. |
| | 48. FElongation | Morphology | The Fmax / Fmin. |
| | 49. Energy | Morphology | A measure of the variation of the intensity of an object. |
| | 50. Mean Energy | Morphology | The average variation in intensity of an object. |
| 30 | 51. Density | Morphology | The accumulation of the number of variations divided by the area. |
| | 52. Density Sum | Morphology | The sum of all the variations within an object. |
| | 53. Unique Track Index | Cell-specific Delimiter | A unique number for a track in a series. |
| | 54. Track Size | Cell-specific Delimiter-Motility | The length of a track. |
| 35 | 55. Track Boundary (pixels) | Cell-specific Delimiter- Motility | A box, in pixels that bounds the track. |

| | | |
|---|---|---|
| 56. Fluorescent marker 1 | Selected protein expression marker for phenotype | The intensity sum of an object, based on a fluorescent marker, TRITC.<br>Note: Filter sets for detecting various fluorophore can be purchased from: Chroma Technical Corp. 72 Cotton Mill Hill, Unit A9 Brattleboro VT 05301, USA |
| 57. Fluorescent marker 2 | Selected protein expression marker for phenotype | The intensity sum of an object, based on a fluorescent marker FITC. |
| 58. Fluorescent marker 3 | Selected protein expression marker for phenotype | The intensity sum of an object, based on a fluorescent marker DAPI. |
| 59. Fluorescent marker 4 | Selected protein expression marker for phenotype | The intensity sum of an object, based on a fluorescent marker CY5. |
| 60. Proximity(Cell to cell contact) | cell-cell interactions (e.g. antigen presentation) | The number of cells that interact or touch a second cell, based on a distance from the perimeter parameter. |
| 61. Frequency of Proximity | cell-cell interactions (e.g. antigen presentation) | The rate of cells touching a second cell. |
| 62. Duration of Proximity | cell-cell interactions (e.g. antigen presentation) | How long the cells stay in contact with a second cell. |
| 63. Cell-Specific Proximity | cell-cell interactions (e.g. antigen presentation) | The number of cells interacting with a second cell of a specified morphology. |
| 64. Phagocytosis Attachment | cell-cell interactions (e.g. antigen presentation) | The number of fluorescent beads (antigens) that are attached to a cell. |
| 65. Phagocytosis Engulfed | cell-cell interactions (e.g. antigen presentation) | The number of fluorescent beads (antigens) inside a cell. |
| 66. Phagocytosis Attachment Area | cell-cell interactions (e.g. antigen presentation) | The area of fluorescent beads (antigens) that are attached to a cell. |
| 67. Phagocytosis Engulfed Area | cell-cell interactions (e.g. antigen presentation) | The area of fluorescent beads (antigens) inside a cell. |

What is claimed is:

1. A method for analyzing 3D motion of cells comprising the steps of:
   placing cells in a solution having a methyl cellulose concentration on a plate having between 6 and 9,600 wells with corresponding volumes of approximately 1 to 4% of the total volume of the solution; and
   imaging a first well of the plate by visible light tracking; taking pictures of a second well of the plate; tracking a third well of the plate by fluorescence, and taking a focal stack of a fourth well of the plate to review 3D motion in the fourth well.

2. A method for analyzing cellular performance comprising the steps of:
   imaging at least one cell in a solution in a first well of a plate having a methyl cellulose concentration of approximately 1 to 4% of the total volume of the solution with visible light to form a first image;
   imaging the cell in the well by fluorescent light to form a second image; and
   overlaying the first and second images.

3. A method as described in claim 2 including the step of taking successive fluorescent images over time and analyzing the successive images to determine cellular performance.

4. A method as described in claim 2 including the step of taking successive visible images over time and analyzing the successive images to determine cellular performance.

5. A method as described in claim 2 including the step of taking multiple visible and fluorescent images over time and overlaying them on one another and differences between successive overlaid images are analyzed to determine cellular performance.

6. A method as described in claim 3 including the steps of taking differences between the images and analyzing them to produce time related kinetic information on cellular performance.

7. A method as described in claim 6 wherein the kinetic information on cellular performance includes information on the effect of proteins and/or other biological or chemical moieties on cellular performance.

8. A method as described in claim 6 wherein the measurement of cellular performance is performed based upon a statistical analysis of time-related and kinetic parameters.

* * * * *